United States Patent

Hohlweg et al.

Patent Number: 5,177,077
Date of Patent: Jan. 5, 1993

[54] 1,4-DISUBSTITUTED PIPERAZINES

[75] Inventors: Rolf Hohlweg, Kvistgaard; Erling Guddal, Brondby; Erik Nielsen, Vaerlose, all of Denmark

[73] Assignee: Novo Nordisk A/S, Bagsvaerd, Denmark

[21] Appl. No.: 728,492

[22] Filed: Jul. 11, 1991

[30] Foreign Application Priority Data

Jul. 26, 1990 [DK] Denmark .............................. 1784/90

[51] Int. Cl.$^5$ .................. A61K 31/495; C07D 409/14; C07D 409/12
[52] U.S. Cl. ..................................... 514/252; 544/379
[58] Field of Search ......................... 544/379; 514/252

[56] References Cited

U.S. PATENT DOCUMENTS

| | | | |
|---|---|---|---|
| 4,096,259 | 6/1978 | Buzas et al. | 544/357 |
| 4,766,215 | 8/1988 | Abou-Gharbia et al. | 544/316 |
| 4,866,062 | 9/1989 | Tóth et al. | 514/255 |
| 4,868,184 | 9/1989 | Tóth et al. | 514/255 |
| 4,874,765 | 10/1989 | Lapis et al. | 514/255 |
| 4,908,365 | 3/1990 | Buzas et al. | 514/252 |

FOREIGN PATENT DOCUMENTS 0099148 1/1984 European Pat. Off.
1529782 10/1978 United Kingdom.
1545094 5/1979 United Kingdom.

OTHER PUBLICATIONS

Kilbourn et al, Chemical Abstracts, vol. 112, No. 73006 (Abstract for Nucl. Med. Biol. 16 pp. 681-686 (1989).
Rueger et al, Chemical Abstracts, vol. 111, No. 57757 (1989) (Abstract for DE 3,726,068, Feb. 16, 1989).
Michael R. Kilbourn, Nucl. Med. Biol., vol. 16, No. 7, pp. 681-686 (1989).

Primary Examiner—Mukund J. Shah
Assistant Examiner—E. Bernhardt
Attorney, Agent, or Firm—Steve T. Zelson; Elias J. Lambiris

[57] ABSTRACT

A disubstituted piperazine compound having the formula I

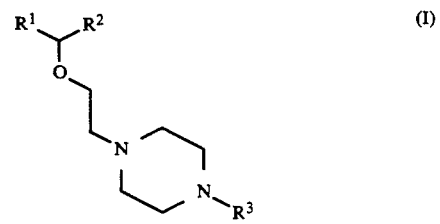

wherein $R^1$ is thienyl or phenyl, which may be substituted with $C_{1-6}$-alkyl or halogen, and $R^2$ is thienyl, which may be substituted with $C_{1-6}$-alkyl or halogen, and $R^3$ is $C_{1-8}$-alkyl, $C_{3-8}$-alkenyl or $C_{3-8}$-cycloalkyl which all may be substituted with hydroxy, oximino or keto in any position giving a stable tertiary amine or $R^3$ is $C_{1-8}$-alkyl or $C_{3-8}$-alkenyl which in any position may be substituted as above, but is terminally substituted with phenoxy, phenyl, thienyl, furyl, methoxy or —CN and pharmaceutically acceptable acid addition salts thereof.

The compounds are useful in the treatment of mental disorders in which a dopaminergic deficit is implicated.

5 Claims, No Drawings

1,4-DISUBSTITUTED PIPERAZINES

This invention concerns novel thiophene-substituted arylalkoxyalkylpiperazines useful for their inhibitory activity at dopamin uptake sites, methods of preparing the same, pharmaceutical compositions containing them and their use for treating mental disorders as e.g. depression and other CNS-related diseases as Parkinson's disease.

Benzhydrylpiperazines, where the benzhydryl group is connected to the nitrogen of a piperazine over a —O—(CH$_2$)n— moiety are known from the German patent publication No. DOS 2719246, where spasmolytic and antiemetic activity is claimed. Further more, in U.S. Pat. No. 4766215 and European patent application No. 0254627 similar benzhydrylethers are described as antihistaminic compounds; German patent publication No. DOS 3726068 claim calcium antagonistic activity for compounds with the aforementioned general structure. Other compounds with the mentioned general structure are also described in European patent application Nos. 0243903, 0243904, 0243905, in GB No. 1545094 and Dutch patent application No. NL 8202636 and claimed to be useful in case of degeneration or hypofunction of the dopaminergic system.

In U.S. Pat. No. 4,096,259, similar compounds bearing polar carbonyl- or alkoxycarbonyl groups are described as central stimulants, however, no dopaminergic activity is claimed or evident from the patent description. Generally the compounds mentioned in the different patent specifications vary greatly with reference to the substitution of the second piperazinenitrogen and thus may give rise to the great variety in pharmacological activity.

It has now unexpectedly been found that by introducing a thiophene- instead of a phenylsubstituent, new and potent DA-uptake inhibitory substances can be obtained. It is expected that such substances possess antidepressant, antiparkinson, antipsychotic, antispastic, memory enhancing as well as other similarly useful therapeutic effects in diseases in which a dopaminergic deficit is implicated. The substances may also have beneficial effects against drug craving or drug abuse.

A disubstituted piperazine compound having the formula I:

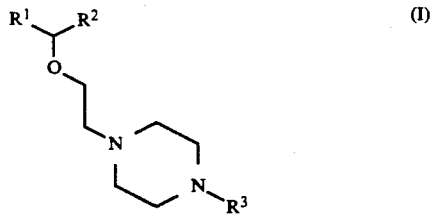

wherein $R^1$ is thienyl or phenyl, which may be substituted with $C_{1-6}$-alkyl or halogen, and $R^2$ is thienyl, which may be substituted with $C_{1-6}$-alkyl or halogen, and $R^3$ is $C_{1-8}$- alkyl, $C_{3-8}$-alkenyl or $C_{3-8}$-cycloalkyl which all may be substituted with hydroxy, oximino or keto in any position giving a stable tertiary amine or $R^3$ is $C_{1-8}$-alkyl or $C_{3-8}$-alkenyl which in any position may be substituted as above, but is terminally substituted with phenoxy, phenyl, thienyl, furyl, methoxy or —CN and pharmaceutically acceptable acid addition salts thereof.

The compounds of formula I may exist as geometric and optical isomers and all isomers and mixtures thereof are included herein. Isomers may be separated by means of standard methods such as chromatographic techniques or fractional crystallization of suitable salts.

Pharmaceutically acceptable acid addition salts of compounds of formula I include those derived from inorganic or organic acids such as hydrochloric, hydrobromic, sulfuric, phosphoric, acetic, lactic, maleic, phthalic and fumaric acid.

The invention also relates to a method of preparing the above mentioned compounds. This method comprises:

a) reacting a compound of formula II

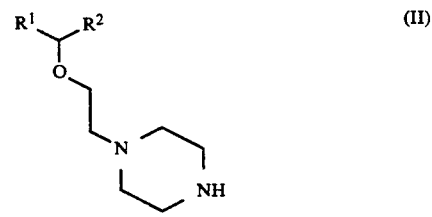

where $R^1$ and $R^2$ have the meanings defined above with a reactive reagent containing the group $R^3$ as defined above, or groups that may be converted to $R^3$ by generally known methods.

Generally known alkylation methods for secondary amines are for example:

1) reaction of the monosubstituted compound of formula II with an alkyl halide or tosylate.

2) addition of the monosubstituted piperazine compound of formula II to a reactive double bond or epoxide.

3) acylation of the monosubstituted piperazine compound of formula II by known methods followed by reduction to yield the desired tertiary amine of formula I.

Compounds of formula II may be prepared by reacting 1-(2-hydroxyethyl)piperazine with a compound of formula V

wherein $R^1$ and $R^2$ have the meanings defined above, and X means hydroxy or halogen applying standard methods of ether synthesis, consisting in a condensation reaction with the removal of water or hydrogen halide.

Compounds of the formula V may be prepared by reacting a compound of formula $R^1$—CHO with a compound $R^2$—MgBr or a compound of formula $R^2$—CHO with a compound of formula $R^1$—MgBr under standard Grignard conditions, and optionally substitute the hydroxy group with halogen applying standard methods of halogenation of hydroxy groups.

b) reacting a compound of formula III

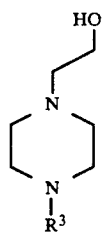

(III)

prepared by alkylation of 1-(2-hydroxyethyl)-piperazine according to one of the aforementioned methods, and thereafter combining this disubstituted piperazine with a compound of formula V

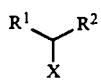

(V)

as described above.

c) reacting a compound of the formula IV

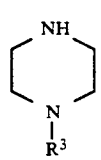

(IV)

prepared by alkylating piperazine according to generally well known methods such as described in section a) and b) above for introducing the group $R^3$, with an optionally substituted diarylmethoxyethyl derivative of formula VI

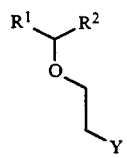

(VI)

where $R^1$ and $R^2$ have the meanings defined above and Y means halogen to obtain the desired compound of formula I. Compounds of formula VI may be prepared by reacting a compound of formula V with haloethanol applying standard methods of ether synthesis.

The biological properties of the compounds of the present invention can be illustrated with the following results:

Biochemistry

Test 1

The compounds were tested for their ability to inhibit the binding of 3H-GBR 12935 to the DA-uptake complex in a striatal membrane preparation following the method described by Andersen (Eur. J. Pharmacol. 166: 493-504, 1989).

Pharmacology

The compounds were also tested for their ability to increase the motility of mice following intravenous administration using the method outlined below.

Test 2

Subjects

Male NMRI mice are used (20±2 g). The animals are housed 20-30 per cage under constant temperature (20°±1°) and relative humidity (40-60%). The animals are brought into the experimental room in the afternoon, the day before they undergo testing.

Methods

The experimentally-naive mice are acclimatized by being placed in a plexiglass box (WLH: 20×20×38 cm), four per box, for a 120 min period, and then treated with the test compound whereafter they are replaced in the plexiglass box.

The plexiglass box is equipped with a frame of photocells (spaced equidistantly) which are situated so as to detect locomotor behaviour of the animals (1 cm above the floor). The photocell chamber is housed in an sound-insulated, dimly-lit, ventilated chest. As a measure of exploratory behaviour, the number of photocell crossings in a 360 min period is detected using a minicomputer. Testing is made between 7:00 and 17.00 h.

Drug Testing

Drugs are administered orally simultaneously with start of testing; N=4/dose; 4-5 doses of test drug is given in a volume of 10 ml/kg.

Results

Computer programmed log-probit methods are used to generate an $ED_{50}$ in mg/kg using as minimum the control result, and as maximum values are used 7700 (this latter value has been experimentally found as the maximum motility counts after d-amphetamine in a 20 min period).

The test result is the lowest $ED_{50}$ value determined at a 20 min interval during the 360 min test period.

Test results obtained by testing some compounds of the invention appear from the following table 1:

TABLE 1

| Example | Test 1 (nM) | Test 2 (mg/kg) |
|---------|-------------|----------------|
| No. 1   | 9           | 30             |
| No. 2   | 4.7         | 17.4           |
| No. 3   | 3.7         | 32             |

The pharmaceutical preparations or compositions comprising the compounds of the invention may be administered to humans or animals by oral or parenteral route.

An effective amount of the active compound or a pharmaceutically-acceptable salt thereof may be determined in accordance with the usual factors, such as the nature and severity of the condition and the weight of the mammal requiring treatment.

Conventional excipients are such pharmaceutically-acceptable organic or inorganic carrier substances suitable for parenteral or enteral application which do not deleteriously react with the active compounds.

Examples of such carriers are water, salt solutions, alcohols, polyethylene glycols, polyhydroxyethoxylated castor oil, gelatine, lactose, amylose, magnesium stearate, talc, silicic acid, fatty acid monoglycerides and diglycerides, pentaerythritol fatty acid esters, hydroxymethylcellulose, and polyvinylpyrrolidone.

The pharmaceutical preparations can be sterilized and mixed, if desired, with auxiliary agents, such as lubricants, preservatives, stabilizers, wetting agents, emulsifiers, salt for influencing osmotic pressure, buffers and/or coloring substances and the like, which do not deleteriously react with the active compounds.

Injectable solutions or suspensions, preferably aqueous solutions with the active compound dissolved in polyhydroxylated castor oil, are particularly suitable for parenteral administration.

Ampoules are convenient unit dosage forms.

Tablets, dragees, or capsules containing talc and/or a carrier or binder or the like are particularly suitable for oral administration. The carrier preferably is lactose and/or corn starch and/or potato starch.

A syrup, elixir, or the like can be used in the cases where a sweetened vehicle can be employed or is desired.

Generally, the compounds of this invention are dispensed in unit dosage form comprising 50-200 mg of active ingredient in or together with a pharmaceutically-acceptable carrier per unit dosage.

The dosage of the compounds according to this invention is 1-500 mg/day, e.g., about 100 mg per dose, when administered to patients, e.g., humans, as a drug.

A typical tablet which may be prepared by conventional tabletting techniques contains:

| | |
|---|---|
| Core: | |
| Active compound (as free compound or salt thereof) | 100 mg |
| Colloidal silicon dioxide (Aerosil ®) | 1.5 mg |
| Cellulose, microcryst. (Avicel ®) | 70 mg |
| Modified cellulose gum (Ac-Di-Sol ®) | 7.5 mg |
| Magnesium stearate | 1 mg |
| Coating: | |
| HPMC approx. | 9 mg |
| *Mywacett ® 9-40 T approx. | 0.9 mg |

*Acylated monoglyceride used as plasticizer for film-coating

The compounds of the invention, together with a conventional adjuvant, carrier, or diluent, may be placed into the form of pharmaceutical compositions and unit dosages thereof, and in such form may be employed as solids, such as tablets or filled capsules, or liquids, such as solutions, suspensions, emulsions, elixirs, or capsules filled with the same, all for oral use, in the form of suppositories for rectal administration; or in the form of sterile injectable solutions for parenteral (including subcutaneous) use. Such pharmaceutical composition and unit dosage forms thereof may comprise conventional ingredients in conventional proportions, with or without additional active compounds or principles, and such unit dosage forms may contain any suitable effective DA-uptake inhibitory amount of the active ingredient commensurate with the intended daily dosage range to be employed. Tablets containing fifty (50) milligrams of active ingredient or, more broadly, ten (10) to two hundred (200) milligrams, per tablet, are accordingly suitable representative unit dosage forms.

Due to their high degree of DA-uptake inhibitory activity and their low toxicity, together presenting a most favorable therapeutic index, the compounds of the invention may be administered to a subject, e.g., a living animal body, in need of such treatment, elimination, alleviation, or amelioration of an indication which is sensitive to a change in the neuronal reuptake of dopamine, often preferably in the form of a non-toxic acid addition salt thereof, e.g. a hydrohalide, especially hydrochloride and hydrobromide or a sulfate, nitrate, phosphate and the like, or an organic salt as acetate, propionate, lactate, malonate, succinate, maleate, fumarate, citrate and the like, concurrently, simultaneously, or together with a pharmaceutically- acceptable carrier or diluent, especially and preferably in the form of a pharmaceutical composition thereof, whether by oral, rectal, or parenteral (including subcutaneous) route, in an effective amount. Suitable dosage ranges are 50-200 milligrams daily, preferably 50-100 milligrams daily, and especially 70-100 milligrams daily, depending as usual upon the exact mode of administration, form in which administered, the indication toward which the administration is directed, the subject involved and the body weight of the subject involved, and the preference and experience of the physician or veterinarian in charge. Such method of treating may be described as the treatment of an indication caused by or related to the dopamine-system in a subject in need thereof, which comprises the step of administering to the said subject a neurologically- or neuroleptically-effective amount of a DA-uptake inhibitory compound of the invention.

The invention will now be described in further detail with reference to the following examples.

EXAMPLE 1

1-[2-((4-fluorophenyl-(3-methyl-2-thienyl)methoxy)ethyl]-4-(3-phenylpropyl)piperazine 3.0 g (0.022 mol) potassium carbonate were added to a stirred solution of 1.5 g (0.006 mol) 4-(3-phenylpropyl)-1-piperazineethanol (GB Pat. No. 1545094) and 2.41 g (0.010 mol) (4-fluorophenyl)(3-methyl-2-thienyl)-methyl chloride (e.g. German patent appl. DE 3726068) in 50 ml acetone. The mixture was refluxed for 2 h, then cooled and diluted with toluene (100 ml). The solution was washed twice with water and once with brine. Evaporation of the organic layer in vacuo yielded an oil, which was redissolved in 50 ml acetonitrile and treated with a solution of maleic acid in acetonitrile. The precipitate was filtered off, washed with diethylether and dried. Recrystallization from ethanol gave 2.88 g (70% of theoretical yield) of the title compound as the dimaleate salt, white solid, m.p. 146°-47° C.

NMR (400 mHz) in DMSO-d$_6$: [ppm]: 1.86 (m) 2H; 2.16 (s) 3H; 2.3-3.3 (m) 14H; 3.55 (m) 2H; 5.78 (s) 1H; 6.15 (s) 4H; 6.83 (d) 1H; 7.15-7.5 (m) 10H.

| | | | |
|---|---|---|---|
| Calculated for $C_{35}H_{41}FN_2O_9S$: | C 61.39, | H 6.03, | N 4.09% |
| Found: | C 61.23, | H 6.11, | N 4.09% |

EXAMPLE 2

1-[2-((4-fluorophenyl)-(2-thienyl)methoxy)ethyl]-4-[3-(2-furyl)-2-propenyl]piperazine

Step A

To a stirred Grignard complex, previously prepared from 17.5 g (0.10 mol) 1-bromo-4-fluorobenzene and 2.43 g (0.10 mol) magnesium turnings in 50 ml tetrahydrofuran, 8.97 g (0.080 mol) thiophene-2-carboxaldehyde, dissolved in 30 ml tetrahydrofuran, was added dropwise. Upon complete addition the reaction mixture was refluxed for 1 h and then poured on a mixture of ice and 6N hydrochloric acid. Subsequent extraction with toluene, washing of the organic layer and evaporation in vacuo, gave 18 g of the desired (4-fluorophenyl)(2-thienyl)methanol as a brown oil. This was directly converted to the corresponding (4-fluorophenyl)(2-thienyl)methyl chloride with thionyl chloride by a procedure known to the art.

Step B 5.0 g (0.036 mol) 3-(2-furyl)acrylic acid was suspended in 100 ml toluene, followed by addition of 7.9 ml (0.108 mol) thionyl chloride. The mixture was refluxed for 1 h, cooled, evaporated and the residue stripped twice with toluene. The resulting acylchloride was redissolved in 25 ml toluene and added dropwise to a solution of 4.7 g (0.036 mol) 1-piperazineethanol in 25 ml toluene and 25 ml pyridine. The reaction mixture was stirred at reflux temperature for 1 h, then cooled, diluted with toluene and washed successively with one portion of 1N sodium hydroxide and three portions of water. Evaporation in vacuo left 3.4 g of an amber oil, which was redissolved in 75 ml of tetrahydrofuran and added dropwise to a solution of 1.32 g (0.035 mol) lithium aluminium hydride in 75 ml of tetrahydrofuran. The reaction mixture was stirred at room temperature for 1 h, cooled in an ice bath and hydrolyzed by dropwise addition of water. The precipitate was filtered off and washed with tetrahydrofuran. The filtrate was concentrated in vacuo and the residue redissolved in acetonitrile. A solution of maleic acid in acetonitrile was added and the precipitate collected by filtration. Recrystallization from isopropanol gave the 1-(2-hydroxyethyl)-4-[3-(2-furyl)-2-propenyl]-piperazine as the dimaleate salt, m.p. 165°–67° C.

NMR (400 mHz) in DMSO-d$_6$ [ppm] 2.6–3.4 (m) 12H; 3.65 (m) 2H; 5.15 (s) 1H; 6.0 (m) 1H; 6.15 (s) 4H; 6.50 (m) 3H; 7.60 (s) 1H.

| Calculated for C$_{21}$H$_{28}$N$_2$O$_{10}$: | C 53.84, | H 6.03, | N 5.98% |
|---|---|---|---|
| Found: | C 54.11, | H 6.35, | N 5.82% |

Step C 1.16 g (0.0084 mol) potassium carbonate were added to a solution of 1.00 g (0.0042 mol) 1-(2-hydroxyethyl)-4-[3-(2-furyl)-2-propenyl]piperazine and 1.16 g (0.0084 mol) (4-fluorophenyl)(2-thienyl)methylchloride in 50 ml toluene. The mixture was refluxed for 16 h, then cooled, diluted with 50 ml toluene and washed twice with water. The crude product obtained by evaporation in vacuo was chromatographed on silicagel (elution with dichloromethane/methanol/acetic acid 95/5/3). The combined pure fractions were adjusted to pH 12 by addition of 2N sodium hydroxide solution, subsequently washed with water and brine and concentrated in vacuo. The oily residue was redissolved in acetonitrile and precipitated by addition of an excess of a solution of maleic acid in acetonitrile. 0.340 g (12% of the theoretical yield) of the title compound were obtained as the dimaleate salt, m.p. 169°–71° C.

NMR (400 mHz) in DMSO-d$_6$ [ppm] 2.6–3.9 (m) 14H; 5.80 (s) 1H; 6.05 (m) 1H; 6.15 (s) 4H; 6.54 (s) 2H; 6.62 (d) 1H; 6.98 (m) 2H; 7.22 (t) 2H; 7.45 (dd) 2H; 7.50 (d) 1H; 7.68 (s) 1H).

| Calculated for C$_{32}$H$_{35}$FN$_2$O$_{10}$S: | C 58.35, | H 5.36, | N 4.25% |
|---|---|---|---|
| Found: | C 57.88, | H 5.40, | N 4.20% |

EXAMPLE 3

1-[2-((4-fluorophenyl)-(3-thienyl)methoxy)ethyl]-4-(3-phenylpropyl)piperazine

Step A

To a stirred Grignard complex, previously prepared from 7.80 g (0.0446 mol) 1-bromo-4-fluorobenzene and 1.10 g (0.045 mol) magnesium turnings in 50 ml tetrahydrofuran, 5.00 g (0.0446 mol) thiophene-3-carboxaldehyde, dissolved in 50 ml tetrahydrofuran, was added dropwise. Upon completion of the addition, the reaction mixture was refluxed for 1 h and then poured on a mixture of ice and 6N hydrochloric acid. Subsequent extraction with dichloromethane, washing of the organic layer with water and evaporation in vacuo, left 8.50 g of crude (4-fluorophenyl)(3-thienyl)methanol as an oil. Chromatography on silica gel (THF/n-heptane 1:2 as eluent) gave 4.4 g of the pure (4-fluorophenyl)(3-thienyl)methanol, which was directly converted to the (4-fluorophenyl) (3-thienylmethyl chloride with thionyl chloride by a known procedure.

Step B

A mixture of 1.1 g (0.0044 mol) 4-(3-phenylpropyl)-1-piperazine-ethanol, 1.0 g (0.0044 mol)(4-fluorophenyl)-(3-thienyl)methyl chloride (as prepared in step A), 1.22 g (0.0088 mol) potassium carbonate and 50 ml toluene was stirred and heated to reflux for 16 h. The reaction mixture was cooled, diluted with toluene and washed with water. The toluene layer was then extracted with 10% tartaric acid. The aqueous phase was separated and rendered basic by addition of 4N sodium hydroxide in excess and extracted with toluene. Evaporation gave the crude product as an oil, which was purified on a silica column (eluent was toluene/ethanol 2:1). The pure fraction was evaporated, redissolved in diethyl ether and treated with a solution of hydrogen chloride in ether. The precipitate was filtered off and recrystallized from isopropanol. The yield was 0.265 g (=12%) of the title compound as the dihydrochloride. M.p. 212°–15° C.

NMR (400 MHz) in DMSO-d$_6$ [ppm] 2.05 (m) 2H; 2.65 (t) 2H; 2.9–4.1 (m) 14H; 5.64 (s) 1H; 7.0–7.6 (m) 12H.

| Calculated for C$_{26}$H$_{33}$Cl$_2$FN$_2$OS: | C 61.06, | H 6.50, | N 5.48% |
|---|---|---|---|
| Found: | C 61.15, | H 6.65, | N 5.38% |

EXAMPLE 4

1-[2-((4-fluorophenyl-(5-methyl-2-thienyl)-methoxy)ethyl]-4-(2-hydroxy-3-phenoxypropyl)-piperazine

Step A 4.86 g (0.2M) of magnesium metal were suspended in 100 ml of dry tetrahydrofuran, and 4-fluoro-bromobenzene, 35 g (0.2M) dissolved in 25 ml of tetrahydrofuran was added dropwise at such a rate as to keep the reaction mixture at slight reflux. The mixture was heated to reflux until all the metal was dissolved, cooled to 0° C. and 24 g (0.19M) of 5-methyl-2-thiophenealdehyde were added at a temperature below 10° C. Then the mixture was heated to reflux for two h, cooled to room temperature and 53.5 g of ammonium chloride was added. The mixture was stirred for 30 min., 200 ml of toluene and 300 ml of water was added, the aqueous phase was extracted twice with toluene, and the combined toluene phases were washed with water, sodium carbonate, and water, and the toluene evaporated to yield 42 g (99%) of colourless oil, showing H-NMR spectrum in accordance with (4-fluorophenyl-5-methyl-2-thienyl)-carbinol. The purity (HPLC) was 94%, and this product was used without further purification in the next step.

Step B 28.9 g (0.13 M) of the product from Step A were dissolved in 250 ml of dry benzene. 104.7 g (1.3M) of chloroethanol, 0.52 g (13 mM) of 60% sodium hydride in oil, and 65 g of molecular sieves (A 4) were added, and the mixture stirred for 2 h at room temperature. The molecular sieves were removed by filtration, benzene and excess of chloroethanol evaporated to yield 36 g of oil which was purified by distillation in vacuo to yield 26.8 g (72%) of oil with the following physical data:

bp$_{0.01mm}$: 114°–118° C.

H-NMR-data(CDCl3) ppm: 2.4 (s) 3H, 3.6–3.8 (m) 4H, 5.5 (s) 1H, 6.55 (d) 1H, 6.65 (d) 1H, 7.0 (t) 2H, 7.4 (dd) 2H.

| Microanalysis: | C | H | Cl |
|---|---|---|---|
| Calculated for $C_{14}H_{14}OFClS$: | 59.05 | 4.96 | 12.45 |
| Found: | 58.39 | 4.98 | 12.68 |
|  | 58.40 | 4.99 | 12.62 |

Step C 26.8 g (94 mM) of the product from Step B were dissolved in 150 ml of dry pyridine, 14.1 g (94 mM) of sodium iodide and 24.3 g (2.82 mM) of piperazine were added, and the mixture heated at 80° C. for 7 h and left at room temperature overnight. The solvent was evaporated, water and toluene were added, the toluene phase was washed three times with water and evaporated to yield 29.5 g of crude oil. 6.7 g of this oil was treated with 2.52 ml of trimethylchlorosilane and 3.08 ml of triethylamine at room temperature in dry tetrahydrofuran for 16 h, filtered, evaporated, and submitted to distillation in vacuo with 50 mg of sodium bicarbonate added to the distillation still. The fraction with bp;$_{0.07mm}$:166° C. was collected, deprotected by dissolution in methanol and evaporation to yield 4.26 g (63.5%) of colourless oil showing H-NMR spectrum in accordance with the proposed structure: 1-[2-((4-fluorophenyl)-(5-methyl-2-thienyl)-methoxy)-ethyl]piperazine.

Step D 1 g of the product produced in Step C was mixed with 0.9 g of 1,2-epoxy-3-phenoxypropane without solvent and heated at 50° C. for three h. 15 ml of ethanol was added, and thereafter a solution of 0.7 g of maleic acid in 15 ml of ethanol to precipitate the dimaleate salt, which after recrystallization from acetonitril melted at 148°–150° C., and showed H-NMR spectrum and microanalysis in accordance with the title compound as a dimaleate salt.

NMR data (DMSO) ppm: 2.4 (s) 3H, 2.7–3.7 (m) 14H+H2O, 3.9 (m) 2H, 4.2 (m) 1H; 5.6 (broad) 1H; 5.7 (s) 1H; 6.1 (s) 4H; 6.65 (d) 1H; 6.75 (d) 1H; 6.95 (m) 3H, 7.2 (t) 2H, 7.3 (t) 2H, 7.4 (dd) 2H.

| Microanalysis: | C | H | N |
|---|---|---|---|
| Calculated for $C_{35}H_{41}N_2O_{11}FS$: | 58.65 | 5.77 | 3.91 |
| Found: | 58.36 | 5.86 | 4.04 |

EXAMPLE 5

1-(2-[(4-fluorophenyl)-(5-methyl-2-thienyl)-methoxy]-ethyl)-4-(4-cyanobutyl)piperazine 3.91 g (9 mM) of 1-(2-[(4-fluorophenyl)-(5-methyl-thienyl)-methoxy]-ethyl)piperazine (Prepared as described in Example 4, Step C) was dissolved in 10 ml of dry dimethylformamide, 2.2 g (13.5 mM) of 5-bromovaleronitrile and 6.2 g of potassium carbonate were added, and the mixture was stirred at 80° C. for 1 h. To the cooled mixture 50 ml of water and 20 ml of toluene were added, the aqueous phase was extracted twice with toluene, the combined organic phases were washed twice with water, and evaporated to yield 4 g of crude oil. The crude product was dissolved in 20 ml of ethanol and treated with a solution of 2.32 g (20 mM) of maleic acid in 20 ml of ethanol to precipitate the dimaleate salt. This crude salt was isolated and recrystallized from 100 ml of hot acetonitrile, and again crystallized from ethanol to obtain the pure dimaleate salt of the title compound as colourless crystals melting at 164°–165° C., showing H-NMR spectrum and microanalysis in accordance with the proposed structure.

H-NMR data (DMSO) ppm: 1.7 (m) 4H; 2.4 (s) 3H; 2.5–2.6 (m) 4H; 2.8–3.4 (m) 10H+H2O; 3.5 (m) 2H; 5.7 (s) 1H; 6.2 (s) 4H; 6.6 (d) 1H; 6.8 (d) 1H; 7.2 (t) 2H; 7.4 (dd) 2H.

| Microanalysis: | C | H | N | S |
|---|---|---|---|---|
| Calculated for $C_{31}H_{38}N_3O_9FS$: | 57.49 | 5.91 | 6.49 | 4.95 |
| Found: | 56.96 | 6.05 | 6.73 | 4.47 |

EXAMPLE 6

1-(2-[(4-fluorophenyl)-(5-methyl-2-thienyl)-methoxy]-ethyl)-4-(2-hydroxy-cyclohexyl)piperazine 1 g of 1-(2-[(4-fluorophenyl)-(5-methylthienyl)-methoxy]-ethyl)piperazine (Prepared as described in Example 4, Step C) was dissolved in 3 ml of cyclohexene oxide, and the mixture heated at 100° C. for 24 h. The excess of epoxide was removed in vacuo, the residue was dissolved in ethanol, treated with charcoal (Norit ® SU 18), filtered, and precipitated as the dimaleate salt by addition of 0.7 g of maleic acid dissolved in 15 ml of ethanol. The crude salt was recrystallized from 65 ml of hot acetonitrile to yield 1.24 g of colourless crystals melting at 162°–164° C., and showing H-NMR spectrum and microanalysis in accordance with the title compound.

H-NMR data (DMSO) ppm: 1.2 (m) 3H; 1.35 (m) 1H; 1.6 (m) 1H; 1.7 (m) 1H; 1.9 (m) 2H; 2.4 (s) 3H; 2.7–3.3 (m) 10H+H2O; 3.5 (m) 3H; 5.7 (s) 1H; 6.2 (s) 4H; 6.6 (d) 1H; 6.7 (d) 1H; 7.2 (t) 2H; 7.4 (dd) 2H.

| Microanalysis: | C | H | N | S |
|---|---|---|---|---|
| Calculated for $C_{32}H_{41}N_2O_{10}FS$: | 57.82 | 6.22 | 4.21 | 4.82 |
| Found: | 57.32 | 6.32 | 4.15 | 4.77 |

| Microanalysis: | C | H | N | S |
|---|---|---|---|---|
| | 57.23 | 6.35 | 4.21 | 4.72 |

EXAMPLE 7

1-(2-[(4-fluorophenyl)-(5-methyl-2-thienyl)-methoxy]-ethyl)-4-(2-hydroxypropyl)piperazine 1 g of 1-(2-[(4-fluorophenyl)-(5-methylthienyl)-methoxy]-ethyl)piperazine (Prepared as described in Example 4, Step C) was dissolved in 3 ml of propylene oxide and heated at reflux for three weeks to complete the reaction. The excess propylene oxide was evaporated, the residue dissolved in 15 ml of ethanol, treated with charcoal (Norit® SU18), filtered, and the crude dimaleate salt of the title compound was precipitated by addition of 0.7 g of maleic acid dissolved in 15 ml of ethanol. This crude precipitate was recrystallized from 20 ml of hot acetonitrile to yield 1.26 g of colourless crystals melting at 150°–152° C., and showing H-NMR spectrum and microanalysis in accordance with the dimaleate salt of the title compound.

H-NMR data (DMSO) ppm: 1.1 (d) 3H; 2.4 (s) 3H; 2.6–3.3 (m) 8H +H$_2$O; 3.5 (m) 2H; 4.0 (m) 1H; 5.2 (m, broad) 1H; 5.7 (s) 1H; 6.2 (s) 4H; 6.6 (d) 1H; 6.7 (d) 1H; 7.2 (t) 2H; 7.4 (dd) 2H.

| Microanalysis: | C | H | N |
|---|---|---|---|
| Calculated for C$_{29}$H$_{36}$N$_2$O$_{10}$FS: | 55.85 | 5.82 | 4.49 |
| Found: | 55.24 | 6.05 | 4.39 |
| | 55.18 | 5.98 | 4.30 |

EXAMPLE 8

1-(2-[Bis-(2,5-dimethyl-3-thienyl)methoxy]ethyl)4-(2-hydroxyethyl)piperazine, dimaleate

Step A 38.2 g (0.20 mol) 3-bromo-2.5-dimethylthiophene was dissolved in 150 ml dry tetrahydrofuran and the solution was cooled to −60° C. 88 ml (0.22 mol) of a 2.5 molar n-butyl lithium solution in hexane was added dropwise to the stirred solution. After 30 min., a solution of 7.4 g (0.10 mol) ethyl formate in 50 ml THF was added. The reaction mixture was stirred at −60° C. for 15 min. and then allowed to warm up to ambient temperature. The reaction mixture was diluted with 300 ml toluene, extracted twice with water, dried over magnesium sulfate and concentrated to 200 ml in vacuo. Then, 50 g molecular sieve (4 Å) and 0.8 g sodium hydride was added to this solution of the intermediate bis-(2,5-dimethyl-3-thienyl)methanol. The mixture was stirred and 80 g (1.0 mol) 2-chloroethanol was added in small portions over a period of 3 h. The reaction mixture was concentrated in vacuo, the residue redissolved in toluene and extracated with three portions of water. Evaporation in vacuo and vacuum distillation furnished the intermediate 1-chloro-2-[bis-(2,5-dimethyl-3-thienyl)-methoxy]ethane as a colourless oil.

Calculated for C$_{15}$H$_{19}$OS$_2$Cl: C 57.21, H 6.08, S 20.86, Cl 11.26%.

Found: C 57.58, H 6.30, S 20.30, Cl 11.56%.

Step B 1.9 g (0.006 mol) of the product of step A was dissolved in 10 ml DMF, 0.9 g sodium iodide and 0.39 g (0.003 mol) 2-hydroxyethylpiperazine was added and the mixture was stirred and heated to 80° C. for one h. After cooling to room temperature the reaction mixture was diluted with toluene, washed once with sodium bicarbonate solution and twice with water. The solvent was evaporated, the residue redissolved in ethanol and the title compound precipitated by adding a solution of maleic acid in ethanol. White crystals, m.p. 157°–58° C.

NMR (400 MHz) in DMSO-d$_6$ (ppm): 2.33 (s) 12H; 2.6–3.3 (m) 14H; 3.48 (t) 2H; 3.68 (t) 2H; 5.40 (s) 1H; 6.15 (s) 4H; 6.60 (s) 2H.

Calculated for C$_{29}$H$_{40}$N$_2$O$_{10}$S$_2$: C 54.36, H 6.29, N 4.37%.

Found: C 53.91, H 6.47, N 4.25%.

We claim:

1. A compound which is 1-[2-((4-fluorophenyl)-2-thienyl)methoxy)ethyl]-4-[3-(2-furyl)-2-propenyl]piperazine or a pharmaceutically acceptable salt thereof.

2. A pharmaceutical composition for use in treating a central nervous system ailment in which a dopaminergic deficit is implicated comprising an effective amount of the compound according to claim 1 and a pharmaceutically acceptable carrier or diluent.

3. The pharmaceutical composition according to claim 2 in the form of an oral dosage unit containing about 50–200 mg of the compound.

4. A method of treating a central nervous system alignment in which a dopaminergic deficit is implicated in a subject in need thereof comprising administering an effective amount of the compound according to claim 1.

5. A method of treating a central nervous system ailment in which a dompaminergic deficit is implicated in a subject in need thereof comprising administering the pharmaceutical composition according to claim 2.

* * * * *